United States Patent
Akahoshi

(10) Patent No.: US 10,667,946 B2
(45) Date of Patent: Jun. 2, 2020

(54) PHACOEMULSIFICATION NEEDLE

(75) Inventor: Takayuki Akahoshi, Tokyo (JP)

(73) Assignee: ART, LIMITED, Grand Cayman (KY)

( * ) Notice: Subject to any disclaimer, the term of this patent is extended or adjusted under 35 U.S.C. 154(b) by 663 days.

(21) Appl. No.: 13/008,714

(22) Filed: Jan. 18, 2011

(65) Prior Publication Data
US 2013/0096569 A1 Apr. 18, 2013

Related U.S. Application Data
(60) Provisional application No. 61/295,763, filed on Jan. 18, 2010.

(51) Int. Cl.
*A61F 9/007* (2006.01)
(52) U.S. Cl.
CPC ............ *A61F 9/00745* (2013.01)
(58) Field of Classification Search
CPC .. A61F 9/00745; A61F 9/00763; A61F 9/007; A61F 9/00709; A61F 9/00736; A61F 9/00754; A61B 17/22012; A61B 17/2202; A61B 17/320068; A61B 2017/320072–320096; A61B 2017/320069; A61B 2017/32007–320098; A61C 3/03

USPC .............. 606/167–170; 604/22; 601/2
See application file for complete search history.

(56) References Cited

U.S. PATENT DOCUMENTS

| | | | | |
|---|---|---|---|---|
| 5,725,495 A | * | 3/1998 | Strukel | A61M 1/0043 604/22 |
| 5,993,408 A | * | 11/1999 | Zaleski | A61F 9/00745 604/22 |
| 6,007,555 A | * | 12/1999 | Devine | 606/169 |
| 6,165,150 A | * | 12/2000 | Banko | 604/22 |
| 6,533,750 B2 | * | 3/2003 | Sutton et al. | 604/22 |
| 2004/0199192 A1 | * | 10/2004 | Akahoshi | 606/169 |
| 2006/0052758 A1 | * | 3/2006 | Dewey | 604/272 |
| 2011/0112466 A1 | * | 5/2011 | Dimalanta | 604/22 |

* cited by examiner

*Primary Examiner* — Katherine M Shi
*Assistant Examiner* — Lindsey Bachman
(74) *Attorney, Agent, or Firm* — Wood, Phillips, Katz, Clark & Mortimer

(57) ABSTRACT

A phacoemulsification needle has a polygonally-shaped tip with an axis that is offset from the axis of the needle body. The material forming the tip is non-uniformly distributed, adding to the motion of the tip when it is vibrated torsionally. In one embodiment, the tip has tip wall segments of varying thicknesses. In another embodiment, the tip has a series of external ribs formed on the tip wall segments, on the wall segment, at the apex where adjacent wall segments meet, or both.

22 Claims, 4 Drawing Sheets

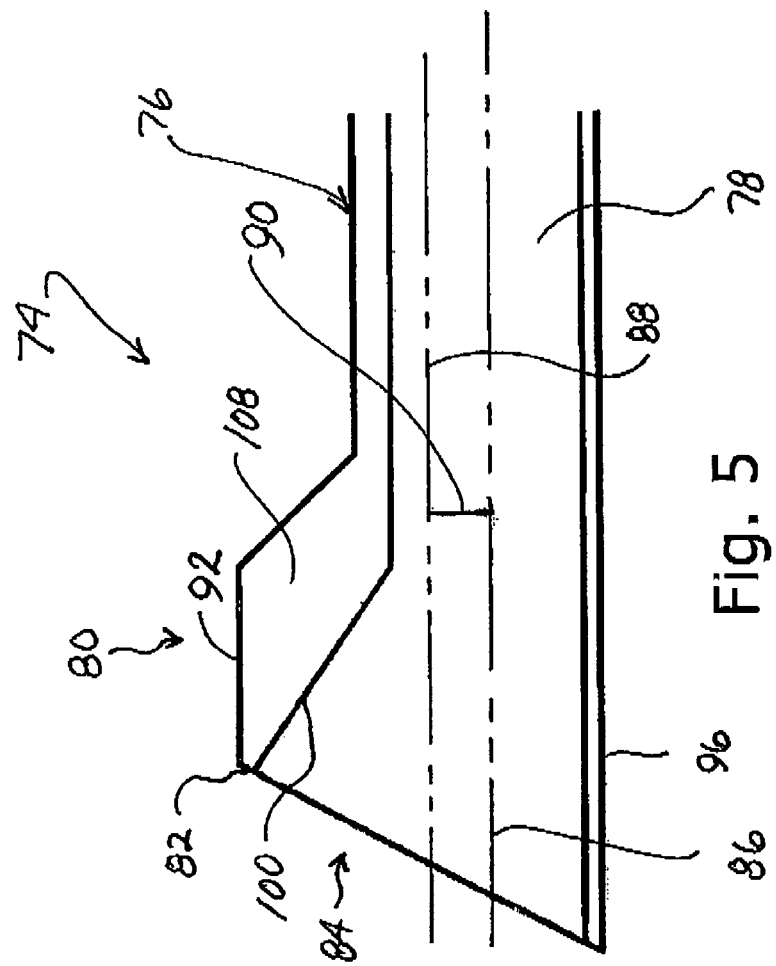
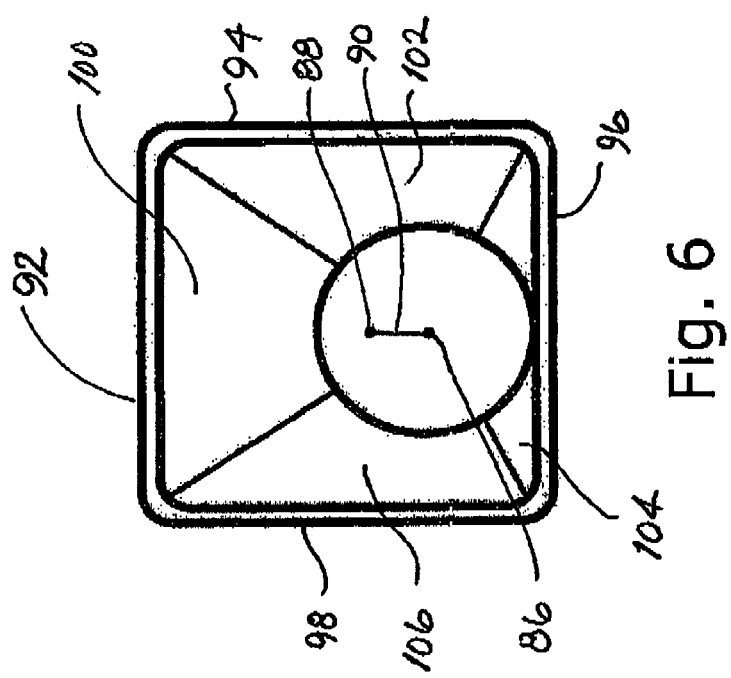

PHACOEMULSIFICATION NEEDLE

This application claims priority from U.S. patent application Ser. No. 61/295,763, filed Jan. 18, 2010 and entitled "Phacoemulsification Needle", which is incorporated herein in its entirety by reference.

FIELD OF THE INVENTION

This disclosure relates to surgical instruments and surgical techniques used in eye surgery and more particularly, to phacoemulsification apparatus and methods for their use.

BACKGROUND OF THE INVENTION

A common ophthalmological surgical technique is the removal of a diseased or injured lens from the eye. Earlier techniques used for the removal of the lens typically required a substantial incision to be made in the capsular bag in which the lens is encased. Such incisions were often on the order of 12 mm in length.

Later techniques focused on removing diseased lenses and inserting replacement artificial lenses through as small an incision as possible. For example, it is now a common technique to take an artificial intraocular lens (IOL), fold it and insert the folded lens through the incision, allowing the lens to unfold when it is properly positioned within the capsular bag. Similarly, efforts have been made to accomplish the removal of the diseased lens through an equally small incision.

One such removal technique is known as phacoemulsification. A typical phacoemulsification tool includes a handpiece to which is attached a hollow needle. Electrical energy is applied to vibrate the needle at ultrasonic frequencies in order to fragment the diseased lens into small enough particles to be aspirated from the eye through the hollow needle. Commonly, an infusion sleeve is mounted around the needle to supply irrigating liquids to the eye in order to aid in flushing and aspirating the lens particles.

It is extremely important to properly infuse liquid during such surgery. Maintaining a sufficient amount of liquid prevents collapse of certain tissues within the eye and attendant injury or damage to delicate eye structures. As an example, endothelial cells can easily be damaged during such collapse and this damage is permanent because these cells do not regenerate. One of the benefits of using as small in incision as possible during such surgery is the minimization of leakage of liquid during and after surgery and the prevention of such a collapse.

Phacoemulsification needles and tips are well represented in the prior art. Needles and tips of varying configurations are well known. A particular shape for a tip or needle is often dictated by the type of handpiece with which the needle is to be used.

U.S. Pat. No. 5,725,495 (Strukel et al) teaches and describes a phacoemulsification handpiece, sleeve and tip illustrating a wide variety of tip configurations and needle cross-sectional configurations.

U.S. Pat. No. 6,007,555 (Devine) teaches and describes an ultrasonic needle for surgical emulsification. The needle and its tip are shown in both circular and oval configurations.

U.S. Pat. No. 6,605,054 (Rockley) teaches and describes a multiple bypass port phacoemulsification tip having multiple aspiration ports and a single discharge port to infuse liquid into the eye.

U.S. Pat. No. 5,879,356 (Geuder) teaches and describes a surgical instrument for crushing crystalline eye lenses by means of ultrasound and for removing lens debris by suction which demonstrates the use of a sleeve positioned concentric to the needle and having a pair of discharge ports formed thereon.

U.S. Pat. No. 5,645,530 (Boukhny) teaches and describes a phacoemulsification sleeve, one variation of which has a bellows portion attached to a discharge port ring which directs an annular flow of liquid around the needle and into the eye. The use of the bellows is intended to allow the sleeve to absorb spikes in liquid pressure during the operation.

Published U.S. Patent Application No. 2003/0004455 (Kadziauskas) teaches and describes a bi-manual phacoemulsification needle using separate emulsification and aspiration needles inserted into the eye simultaneously during surgery.

Published U.S. Patent Application No. 2006/0217672 (Chon) teaches and describes a phacoemulsification tip that is swaged or crimped at its distal end. The tip is intended for use with a handpiece producing torsional motion and the crimping forms cutting edges at the distal end.

Many phacoemulsification needles and tips are designed for use with handpieces that vibrate the needle longitudinally at relatively low frequencies. In addition to longitudinal vibration, the NeoSoniX® handpiece sold by Alcon, Inc. of Ft. Worth, Tex. has a rotational or torsional oscillation vibration frequency of about 100 cycles/second. There are also handpieces that provide torsional oscillation of the phacoemulsification tip at frequencies of about 32,000 cycles/second.

U.S. Pat. No. 6,077,285 (Bouhkny) teach and describe a torsional ultrasound handpiece having two sets of piezoelectric crystals, one set arranged to operate the handpiece in a longitudinal mode and the other set arranged to operate the handpiece in a torsional mode.

Use of the torsional-type handpiece has called for phacoemulsification needle tip designs differing from those used with the longitudinal-type handpiece. For example, needles have been designed with tips that are shaped, swaged and angled to take advantage of the torsional motion created by the handpiece.

Many surgeons favor phacoemulsification needles having the straight tip design most commonly used with longitudinal handpieces but have found that using them with torsional handpieces does not produce good results.

I have found that forming the needle tip in an off-axis position relative to the axis of the needle body causes sufficient eccentric motion, or "wobble" during torsional motion to produce improved phacoemulsification results while retaining the straight-tip configuration. Forming the needle body in an asymmetric configuration also produces useful "wobble". I have also determined that use of an off-axis needle tip or needle body improves performance when the needle is used in a non-longitudinal type of handpiece, such as in the torsional mode or the elliptical mode.

In accordance with a preferred embodiment of the apparatus a phacoemulsification needle is provided for use with a high-frequency torsional phacoemulsification handpiece with the needle having a straight needle tip with the tip being formed off-axis with respect to the hollow passage formed through the needle.

In accordance with another preferred embodiment, the needle body is formed with an off-axis central aspiration passageway, a central aspiration passageway with a cross-sectional shape different from that of the needle body, or a combination of these configurations, and combined with a standard or an off-axis needle tip.

While the following describes a preferred embodiment or embodiments of the present invention, it is to be understood that such description is made by way of example only and is not intended to limit the scope of the present invention. It is expected that alterations and further modifications, as well as other and further applications of the principles of the present invention will occur to others skilled in the art to which the invention relates and, while differing from the foregoing, remain within the spirit and scope of the invention as herein described and claimed. Where means-plus-function clauses are used in the claims such language is intended to cover the structures described herein as performing the recited functions and not only structural equivalents but equivalent structures as well. For the purposes of the present disclosure, two structures that perform the same function within an environment described above may be equivalent structures.

BRIEF DESCRIPTION OF THE DRAWINGS

Further aspects of the present invention will be best understood by reference to the accompanying drawings in which like numbers are used to identify like parts, and which are presented to illustrate the aspects of the invention although not necessarily to actual scale, wherein:

FIG. 5 is a lateral sectional view of a second embodiment of a phacoemulsification needle applying certain principles of the present invention;

FIG. 6 is an end view of the needle of FIG. 5;

DETAILED DESCRIPTION OF THE INVENTION

Figure 1:
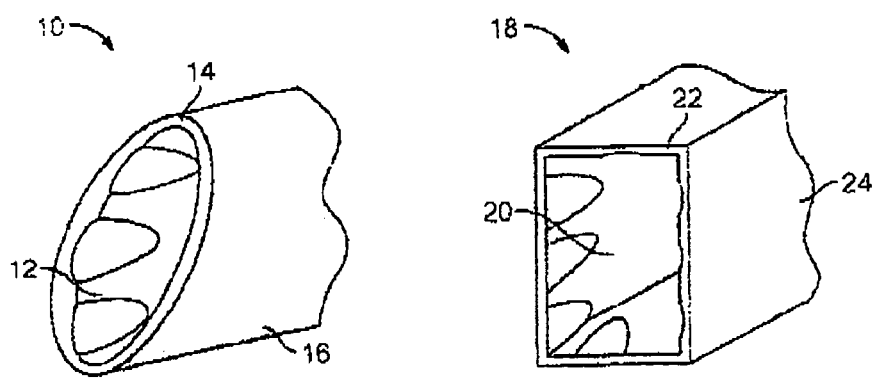
FIG. 1 is a drawing showing prior art straight oval- and square-shaped tips.

Referring now to FIG. 1, the numeral 10 indicates generally a prior art phacoemulsification needle tip as shown in U.S. Pat. No. 6,007,555. Needle 10 terminates in a mouth 12 defined by a lip 14 at the end of needle body 16, with lip 14 and needle body 16 formed as having an oval cross-section configuration.

Referring to FIG. 1, the numeral 18 indicates generally a prior art phacoemulsification needle tip from U.S. Pat. No. 6,007,555, having a mouth 20 defined by a lip 22 at the end of needle 24. The cross-sectional configuration of needle 18 and mouth 20 is a rectangle.

Figure 2:
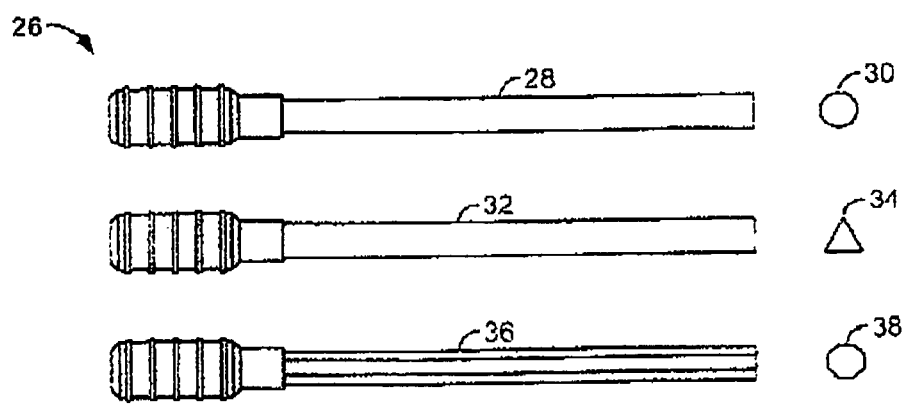
FIG. 2 is a drawing showing several prior art needle cross-sectional configurations.

Referring now to FIG. 2, the numeral 26 identifies several prior art phacoemulsification needles as described in U.S. Pat. No. 5,725,495, with needle 28 having a circular cross-section as shown at 30, needle 32 having a triangular cross-section as shown at 34 and needle 36 having an octagonal cross-section as shown at 38.

Both tips 10 and 18 in FIG. 1 exemplify one form of a "straight" needle tip, that is, a tip that is coaxial with or centered on the hollow aspiration passageway formed through the needle body. Other straight tips are known which have needle tips that are flared, that is, larger in cross-sectional area than the needle's aspiration passageway yet which are centered on the passageway.

Figure 3:
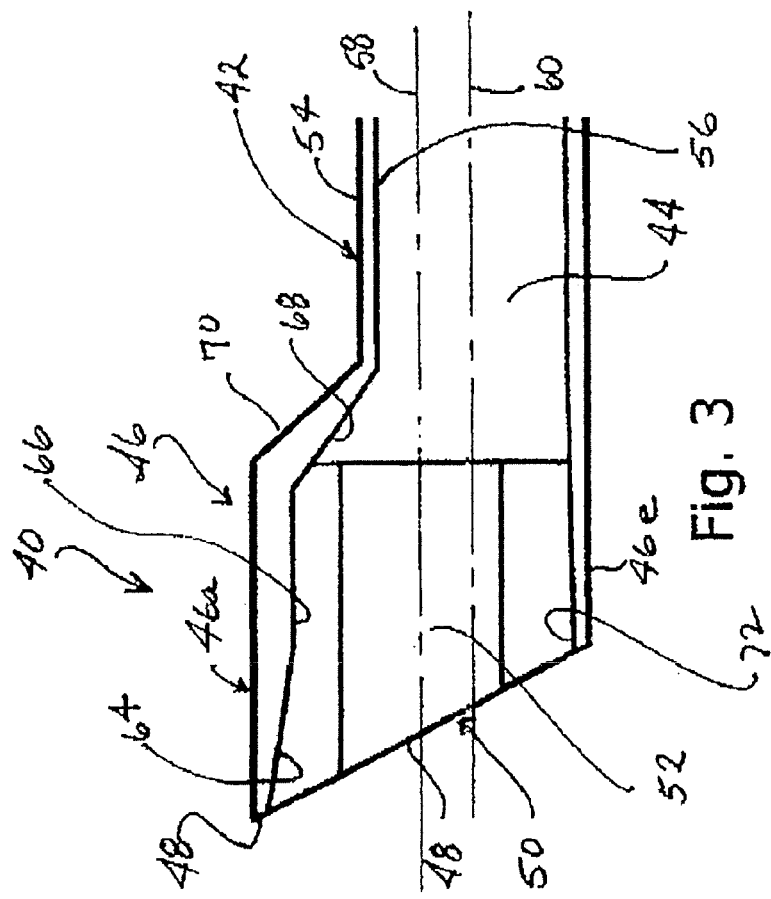
FIG. 3 is a lateral sectional view of a portion of a phacoemulsification needle constructed in accordance with certain principles of the present invention.

Referring now to FIG. 3, the numeral 40 indicates, generally, a phacoemulsification needle embodying certain aspects of the present invention. Needle 40 has a hollow needle body 42 through which an aspiration passageway 44 is formed. Needle 40 terminates at a tip 46 having a lip 48 which defines a tip mouth 50. Tip 46 is hollow having a tip cavity 52 which communicates with aspiration passageway 44.

Figure 4:
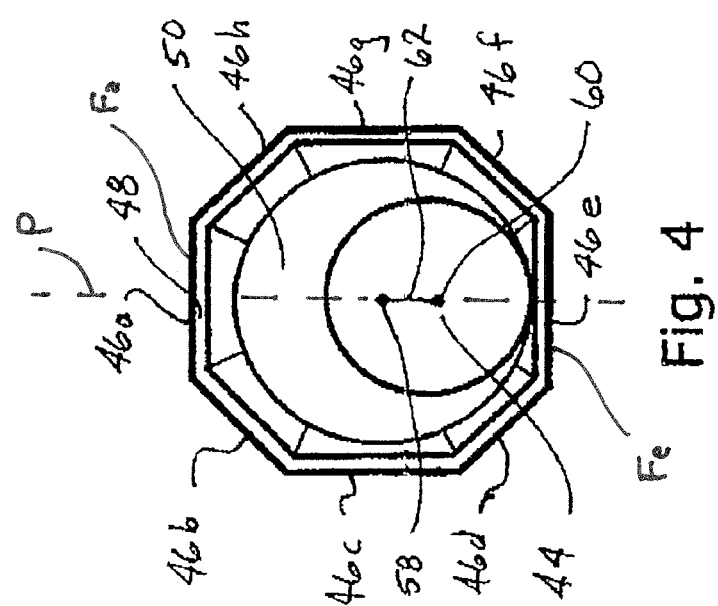
FIG. 4 is an end view of the needle of FIG. 3.

As seen in FIG. 4, tip 46 is formed with an octagonal cross-sectional shape having outer tip wall segments 46a, 46b, 46d, 46e, 46f, 46g, and 46h.

As further seen in FIGS. 3 and 4, tip 46 has a central axis 58 while a needle body 42 has a central axis 60. In the embodiment shown, needle axis 58 is offset from tip body axis 60 by an offset distance 62.

Offset 62 results from the fact that while a portion of tip 46 is coextensive with a portion of needle body 42, other portions of tip 46 extend past tip body 42. In other words, tip 46 is flared, meaning that a significant portion of the cross-sectional configuration of tip 46 is larger in diameter than that of needle body 42 and that the flare with which tip 46 is constructed is not symmetrical about the needle body 42. As further shown in FIGS. 3 and 4, the needle body 42 has an inner surface 56 defining an inner radius with respect to the body central axis 60. The tip 46 has a generally cylindrical inner surface 72 defining an inner radius with respect to the tip central axis 58. The latter tip radius can be seen as substantially equal to the sum of the needle body radius plus the offset 62 between the central axes 58, 60.

As seen in FIG. 3, tip wall segment 46a has a first inner wall segment 64 which terminates at lip 48 and extends axially in a direction distal from lip 48 at an angle to tip wall segment 46a. First inner wall segment 64 is contiguous with a second inner wall segment 66 which, in this embodiment extends generally parallel to and extending in a rear axial direction from first inner wall segment 64. A third inner wall segment 68 is formed at an angle to second wall segment 66 and extends from second wall segment 62 to needle body 42. In similar fashion, outer wall segment 70 of tip 46 extends at an angle to tip wall segment 46a and terminates at and is integral with needle body 42 with the region between wall segments 68, 70 defining a connecting part. Thus, when tip wall segment 46a, outer wall segment 70 and outer needle body wall segment 54 are contiguous as are inner first wall segment 64, second wall segment 66, third wall segment 68 and inner needle body 56.

As further seen in FIGS. 3 and 4, outer tip wall segment 46e which is diametrically opposite to wall segment 46a is not offset from needle body 42, with inner wall segment 72 of tip 46 being contiguous with inner wall 56 of needle body 42.

As can be appreciated from the drawings, wall segments 46b, 46c and 46d are offset, to varying degrees, from needle body outer wall 54. In like fashion, segments 46f, 46g and 46h are similarly and varyingly offset.

In a preferred embodiment, segment 46e has little or no offset, segments 46d and 46f have identical offsets, being greater than the offset to segment 46e, segments 46c and 46g have identical offsets, said offsets being greater than the offsets to segments 46d and 46f, segments 46b and 46h have identical offsets with said offsets being greater than the offsets of segments 46c and 46g, and 46a has an offset greater than the offsets for segments 46b and 46h.

As further seen in FIG. 3, the portion of tip 40 defined by segments 46a, 70, 64, 66 and 68 include a greater amount of tip material than the portion defined by segment 46e and inner surface 56. In like fashion, varying amounts of tip material are contained in segments 46b and 46h, 46c and 46g, and 46d and 46f. This non-uniform distribution of tip material or tip mass makes tip 46 asymmetrical with respect to mass distribution as well as asymmetrical with respect to axis 60 of needle body 42.

Referring now to FIG. 5, a phacoemulsification needle 74 is shown having a hollow needle body 76 through which an aspiration passageway 78 is formed. At the distal end of needle body 76, a needle tip 80 is formed which, as seen in FIG. 5, is flared and has a larger cross-sectional area than needle body 76. Tip 80 terminates at a lip 82 which defines a tip mouth 84.

As seen in FIG. 5, tip body 76 has a central axis 86 while tip 80 has a central axis 88 with axes 86 and 88 being offset by a distance 90.

As seen in FIG. 6, tip 80 has a square cross-sectional shape having tip wall segments 92, 94, 96 and 98 terminating at and communicating with aspiration passageway 78. As seen in FIG. 6, each tip wall segment has a corresponding inner wall portion with tip wall segment 92 having an inner wall portion 100, tip wall segment having an inner wall portion 102, tip wall segment 96 having an inner wall portion 104, and tip wall portion 98 having an inner wall portion 106. As seen in FIG. 5, inner wall portion 100 is formed at an angle to tip axis 88. In like fashion, inner tip wall portions 102 and 106 are formed at angles to tip axis 88 and, in this embodiment, are formed at identical angles while inner wall portion 104 is formed at an angle to tip axis 88 that differs from the angles of inner wall portions 100, 102 and 106.

As seen in FIG. 5, the angle at which inner wall portion 100 is inclined creates a tip body portion 108 differing in size and dimension than the tip wall portions defined by inner wall segments 102, 104 and 106. This configuration results in a non-uniform distribution of tip material which creates a "wobble" effect when needle 74 is vibrated by a phacoemulsification handpiece.

As seen in FIGS. 3-6, the needle embodiments described herein have outer tip wall surfaces which act as cutting or emulsifying surfaces when the tips are moved in a torsional direction. The non-uniform distribution of tip wall material adds to the efficiency of the tip when used in the torsional mode by adding increased torsional motion to the tip.

Figure 7:
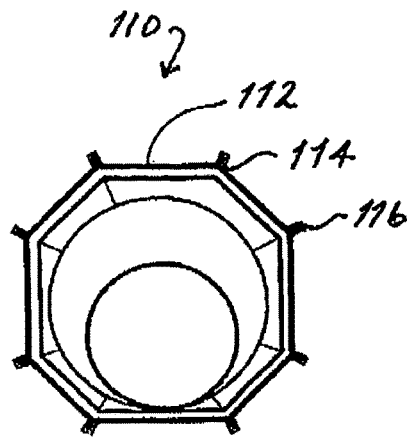
FIG. 7 is an end view of a third embodiment of a phacoemulsification needle applying certain principles of the present invention.

Referring now to FIG. 7, the numeral 110 identifies a needle tip having a generally octagonal configuration such as that shown in FIG. 4. Tip 110 has flats 112, with adjacent flats 112 meeting at apices 114. An octagonal tip will have eight such flats and eight such apices. In the FIG. 4 embodiment each flat makes an obtuse angle substantially greater than 90° with each of the adjacent flats between which it directly resides.

As seen in FIG. 4, a plane P containing the axes 58, 60 extends through the flats Fa, Fe, defined by the wall segments 46a, 46e, respectively. The plane P extends through a midportion of a circumferential width of each of the flats Fa, Fe. The planes of the flats Fa, Fe are substantially parallel to each other and orthogonal to the plane P.

Figure 8:
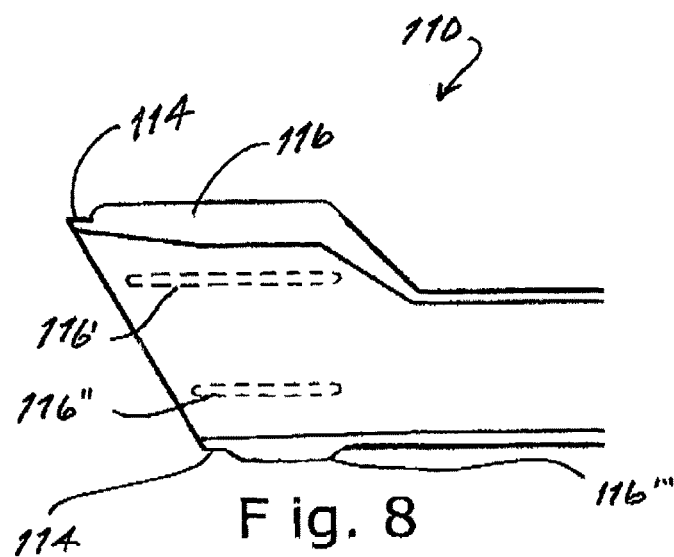
FIG. 8 is a lateral view of the needle of FIG. 7.

In the embodiment shown, an external ridge 116 is formed at each such apex 114. As seen in FIG. 8, ridges 116 are formed integrally with tip 110. It is also possible to form ridges 116 on tip 110 after tip 110 has been manufactured.

As seen in FIG. 7, ridges 116 can be of varying lengths when tip 110 is formed with an angled or Kellman configuration. Thus, ridge 116 is longer than ridge 116' which, in turn, is longer than ridge 116" which, in turn, is longer than ridge 116'.

While tip 110 is shown with an octagonal configuration, various other geometric shapes may also be used, with ridges formed and sized to fit at corresponding apices.

Figure 9:
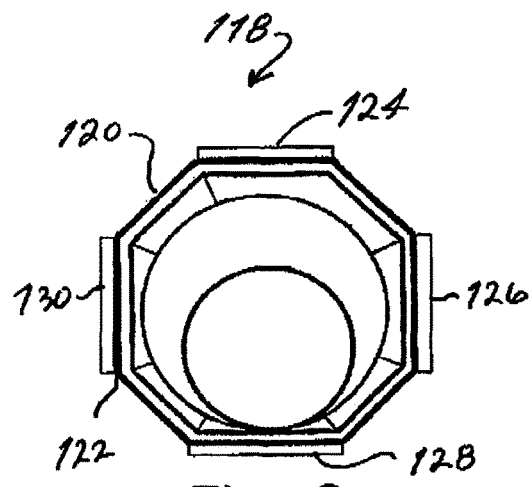
FIG. 9 is an end view of a fourth embodiment of a phacoemulsification needle applying certain principles of the present invention.
Figure 10:
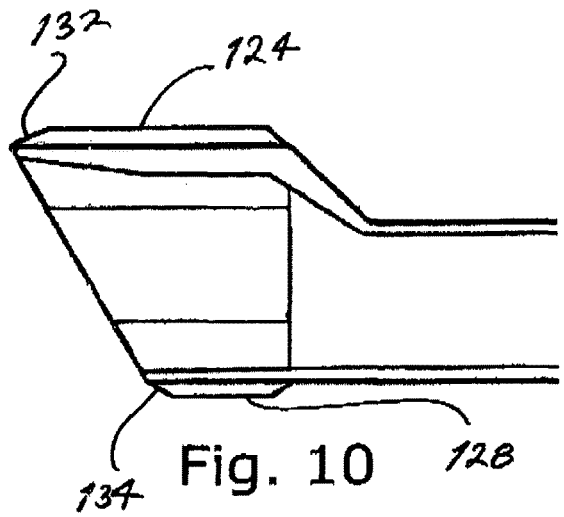
FIG. 10 is a lateral view of the needle of FIG. 9.

Referring now to FIGS. 9 and 10, the numeral 118 identifies generally a needle tip having a generally octagonal shape. Tip 118 has eight flats 120, with adjacent flats meeting at apices 122. As seen in FIG. 9, a series of blocks are formed on selected of flats 20 120. In the embodiment shown, a first block 124 is formed on flat 120', a second block 126 is formed on flat 120", a third block 128 is formed on flat 120''' and a fourth block 130 is formed on flat 120''''. In this embodiment, none of flats 120'-120''' are adjacent to one another.

Each block is formed with a generally rectangular cross-section which rises above 25 its corresponding flat to a selected height and may extend a selected lateral distance between adjacent apices.

As seen in FIG. 10, each block may be tapered at its lead edge. Thus, block 124 has a lead taper 132 and block 128 has a lead taper 134. The blocks shown in FIGS. 9 and 10 are formed on non-adjacent flats: it is also possible to form blocks on selected flats depending upon the cross-sectional configuration 5 of the tip and the desired phaco effect.

It is believed that configurations such as shown in FIGS. 7-10 benefit from having longitudinally-extending external ridges or blocks which have exposed lateral surfaces which, it is believed, increases phaco efficiency when the tip is moved torsionally.

What is claimed is:

1. A phacoemulsification needle for emulsifying body tissue, said needle configured to be attached to a phacoemulsification handpiece configured to impart vibration to said needle, said needle comprising:
    a hollow needle body having a distal end and a proximal end, said needle body having a passageway and a longitudinally-extending central axis and configured to be attachable to a handpiece;
    a hollow needle tip formed at said distal end and having an interior surface defining an opening communicating with said hollow needle body passageway and an exterior surface, said tip having at least four flat wall segments arranged to cooperatively give a part of said tip a polygonal cross-sectional shape greater in size than a cross-section of said needle body, taken normal to said needle body central axis;
    said tip having a central tip axis,
    said tip exterior surface having an outermost radial extent from the needle body central axis,
    said tip axis and said needle body axis being substantially parallel and offset one from the other;
    each said flat tip wall segment terminating at a lip and defining an outer flat,
    each of the flats residing directly between two adjacent other of the flats,
    said tip wall segment lips defining a needle mouth,
    at least one of said flat tip wall segments having a thickness greater than another of said flat tip wall segments, whereby said tissue is emulsified when said needle is vibrated by a phacoemulsification handpiece, wherein each of the flats makes an obtuse angle, substantially greater than 90°, with each of the two adjacent other of the flats between which it resides thereby, defining corners of the tip exterior surface, wherein first and second of the corners reside at the outermost radial extent of the tip exterior surface.

2. The apparatus as recited in claim 1 wherein said cross-sectional shape is square.

3. The apparatus as recited in claim 2 wherein one said tip wall segment is thicker than the remaining segments and is angled outward from said needle body.

4. The apparatus as recited in claim 1 wherein said cross-sectional shape of the part of the tip is octagonal.

5. The apparatus as recited in claim 4 wherein a first of said flat tip wall segments has a first thickness;
a second and a third of said flat tip wall segments are adjacent to said first flat tip wall segment,
each said second and third flat tip wall segments having a second thickness greater than said first thickness;
a fourth flat tip wall segment adjacent to said second flat tip wall segment;
a fifth flat tip wall segment adjacent to said third flat tip wall segment,
said fourth and fifth flat tip wall segments having a third thickness greater than said second thickness;
a sixth flat tip wall segment adjacent to said fourth flat tip wall segment;
a seventh flat tip wall segment adjacent to said fifth flat tip wall segment,
said sixth and seventh flat tip wall segments having a fourth thickness greater than said third thickness; and
an eighth flat tip wall segment joining said sixth and seventh flat tip wall segments,
said eighth flat tip wall segment having a fifth thickness greater than said fourth thickness.

6. The apparatus as recited in claim 5 wherein said first flat tip wall segment is spaced from said needle body axis by a first distance;
each said second and third flat tip wall segments are spaced from said needle body axis by a second distance greater than said first distance;
each said fourth and fifth flat tip wall segments are spaced from said needle body axis by a third distance greater than said second distance;
each said sixth and seventh flat tip wall segments are spaced from said needle body axis by a fourth distance greater than said third distance;
said eighth flat tip wall segment spaced from said needle body axis by a fifth distance greater than said fourth distance.

7. The apparatus as recited in claim 6 wherein said needle body has an interior radius around said needle body axis, and said first distance is substantially equal to said needle body interior radius.

8. The apparatus as recited in claim 1 wherein
each said tip wall segment has an outer surface and an inner surface;
each said tip wall segment outer surface meets the outer surface of an adjacent tip wall segment at an apex; and
at least one rib is formed on the exterior surface of said tip.

9. The apparatus as recited in claim 8 wherein said at least one rib is positioned on one said tip wall segment outer surface.

10. The apparatus as recited in claim 9 wherein said tip has an octagonal cross-sectional shape, and
said tip has four said ribs with one said rib formed on alternating of said tip wall segment outer surfaces.

11. The apparatus as recited in claim 8 wherein said at least one rib is positioned on said tip outer surface at one said apex.

12. The apparatus as recited in claim 11 wherein said tip has an octagonal cross-sectional shape, and
said tip has four said ribs with one said rib formed on alternating of said tip wall segment apices.

13. The apparatus as recited in claim 11 wherein at least one said rib
is formed on at least one said tip wall segment outer surfaces.

14. The apparatus as recited in claim 1, wherein said needle tip has a portion with a cylindrical inner surface centered on said central tip axis.

15. The apparatus as recited in claim 14, wherein said needle body has an inner radius and said tip cylindrical inner surface has a radius substantially equal to the sum of said needle body inner radius plus said offset between said tip axis and said needle body axis.

16. The apparatus as recited in claim 1, in combination with a phacoemulsification handpiece configured to impart torsional vibration.

17. A phacoemulsification needle for emulsifying body tissue, said needle configured to be attached to a phacoemulsification handpiece imparting vibration to said needle, said needle comprising:
a hollow needle body having a distal end and a proximal end, said needle body having a passageway and a longitudinally-extending central axis and attachable to a hand piece;
a hollow needle tip formed of at least four flat wall segments at said distal end and having an interior surface defining an opening communicating with said hollow needle body passageway and an exterior surface;
said tip having a central tip axis substantially parallel to, and offset from, said needle body axis;
said tip exterior surface having an outermost radial extent from the needle body central axis and a plurality of corners where adjacent flat tip wall segments meet:
each of said flat tip wall segments terminating at a lip and defining an outer flat, said lips defining a needle mouth having a polygonal shape as viewed along the central tip axis that is greater in size than the needle body as viewed along the needle body central axis, one of said flat tip wall segments having a thickness greater than a plurality of the flat tip wall segments, whereby said tissue is emulsified when said needle is vibrated,
wherein a first plane containing the longitudinally extending central axis and the central tip axis extends through the one of the flat tip wall segments,
wherein first and second of the corners reside at the outermost radial extent of the tip exterior surface.

18. The apparatus as recited in claim 17 in combination with a phacoemulsification handpiece configured to impart vibration to said needle.

19. The apparatus as recited in claim 17 wherein the polygonal shape has eight sides.

20. The apparatus as recited in claim 17 wherein the one of the flat tip wall segments has a first of the flats that resides in a second plane that is substantially perpendicular to the first plane.

21. The apparatus according to claim 20 wherein the first flat has a circumferential width and the first plane intersects the first flat at a midportion of the circumferential width of the first flat.

22. The apparatus according to claim 20 wherein another of the tip wall segments has a second flat that is substantially parallel to the first flat and through which the first plane extends.

\* \* \* \* \*